United States Patent [19]

Tessier et al.

[11] Patent Number: 4,569,928
[45] Date of Patent: Feb. 11, 1986

[54] ANTI-PARASITIC ESTERS

[75] Inventors: Jean Tessier, Vincennes; André Teche, Paris; Jean-Pierre Demoute, Montreuil-sous-Bois, all of France

[73] Assignee: Roussel Uclaf, Paris, France

[21] Appl. No.: 546,392

[22] Filed: Oct. 28, 1983

[30] Foreign Application Priority Data

Nov. 2, 1982 [FR] France .................................. 82 18328

[51] Int. Cl.$^4$ .......................................... C07D 24/72
[52] U.S. Cl. .................................. 514/66; 514/67; 514/68; 514/351; 514/389; 514/461; 514/464; 514/513; 260/455 R; 548/302; 548/312; 549/420; 549/434; 549/437; 546/300
[58] Field of Search ...................... 514/66, 67, 68, 351, 514/389, 461, 464, 513; 260/455 R; 548/302, 312; 549/420, 434, 437; 546/300

[56] References Cited

U.S. PATENT DOCUMENTS

| B 350,708 | 1/1975 | Henrick et al. | 260/455 R |
|---|---|---|---|
| 3,296,292 | 1/1967 | Richter et al. | 260/455 R |
| 4,216,162 | 8/1980 | Arlt et al. | 260/455 R |
| 4,230,722 | 10/1980 | Malherbe et al. | 260/455 R |
| 4,276,305 | 1/1981 | Suchy | 260/455 R |
| 4,360,375 | 11/1982 | Jikihara et al. | 260/455 R |

Primary Examiner—Joseph L. Schofer
Assistant Examiner—Bernard Lipman
Attorney, Agent, or Firm—Bierman, Peroff & Muserlian

[57] ABSTRACT

Novel esters in all possible isomeric forms and mixtures thereof of the formula

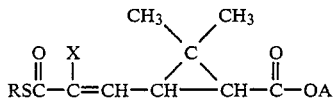

wherein R is selected from the group consisting of (a) optionally unsaturated alkyl of 1 to 18 carbon atoms and optionally unsaturated cycloalkyl or cycloalkylalkyl of 3 to 8 carbon atoms optionally substituted with at least one member of the group consisting of halogen, —OH, —SH, —OR′, —SR′, —NO$_2$,

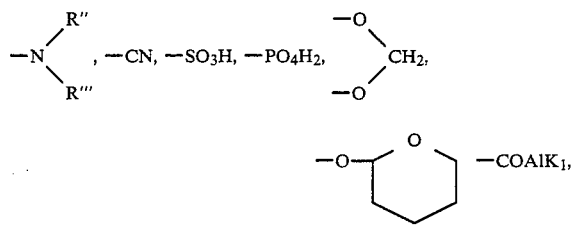

—SO$_2$AlK$_2$, —SO$_3$AlK$_3$, aryl optionally substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

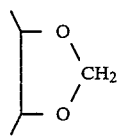

R′ is alkyl of 1 to 8 carbon atoms, R″ and R‴ are individually selected from the group consisting of hydrogen and alkyl of 1 to 8 carbon atoms, AlK$_1$, AlK$_2$ and AlK$_3$ are individually alkyl of 1 to 18 carbon atoms (b) aryl of 6 to 14 carbon atoms optionally substituted with at least one substituent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle optionally substituted with at least one member of the group consisting of —OH, alkoxy of 1 to 8 carbon atoms, alkyl of 1 to 8 carbon atoms, halogen, —CF$_3$, —OCF$_3$ and —SCF$_3$, A is selected from the group consisting of optionally unsaturated alkyl of 1 to 18 carbon atoms, optionally unsaturated cycloalkyl of 3 to 18 carbon atoms and the remainder of an alcohol used in synthesis of pyrethrinoid esters, X is halogen and the ethylenic double bond may have Z or E geometry having antiparasitic activity, especially insecticidal, acaricidal and nematocidal activity.

18 Claims, No Drawings

ANTI-PARASITIC ESTERS

STATE OF THE ART

Certain derivatives of cyclopropane carboxylic acid derivatives are known having in the 3-position the group ROOC—CH=CH— having essentially E geometry. Examples of such prior art are French Patent Nos. 2,185,612, 2,418,218 and 2,143,820, as well as J. Chem. Soc., Perkin I (1974), p. 2470 and Pest. Sci., Vol. 7 (1976), p. 499. Copending U.S. patent application Ser. Nos. 266.164 filed May 22, 1981, now abandoned, and 279,076 filed June 6, 1981, now abandoned, U.S. Pat. No. 4,402,972 and copending U.S. patent application Ser. No. 495,481 filed May 17, 1983, now U.S. Pat. No. 4,489,093, describe related cyclopropane carboxylic acid derivatives.

OBJECTS OF THE INVENTION

It is an object of the invention to provide the novel Z and E isomers of the compounds of formula I as well as a novel process and novel intermediates for their preparation.

It is another object of the invention to provide novel pesticidal compositions and a novel method of killing insects and acariens.

It is a further object of the invention to provide novel compositions and method of combatting scabies and to provide anthelmintic activity.

These and other objects and advantages of the invention will become obvious from the following detailed description.

THE INVENTION

The novel compounds of the invention are esters in all possible isomeric forms of the formula $$\underset{RSC-C=CH-CH}{\overset{O}{\underset{\|}{\phantom{X}}}\,\overset{X}{\underset{|}{\phantom{X}}}}\overset{CH_3\diagdown\phantom{X}\diagup CH_3}{\underset{\diagup\phantom{X}\diagdown}{C}}\underset{CH-C-OA}{\overset{O}{\underset{\|}{\phantom{X}}}} \quad \text{I}$$

wherein R is selected from the group consisting of (a) optionally unsaturated alkyl of 1 to 18 carbon atoms and optionally unsaturated cycloalkyl or cycloalkylalkyl of 3 to 8 carbon atoms optionally substituted with at least one member of the group consisting of halogen, —OH, —SH, —OR', —SR', —NO$_2$,

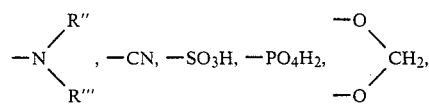, —CN, —SO$_3$H, —PO$_4$H$_2$, 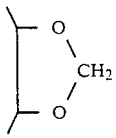

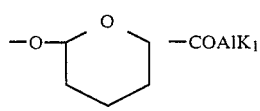

—SO$_2$AlK$_2$, —SO$_3$AlK$_3$, aryl optionally substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

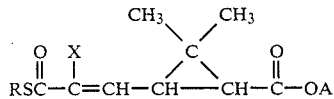

R' is alkyl of 1 to 8 carbon atoms, R" and R'" are individually selected from the group consisting of hydrogen and alkyl of 1 to 8 carbon atoms, AlK$_1$, AlK$_2$ and AlK$_3$ are individually alkyl of 1 to 18 carbon atoms (b) aryl of 6 to 14 carbon atoms optionally substituted with at least one substituent selected from the group consisting of —OH, alkoxy of 1 to 8 carbon atoms, alkyl of 1 to 8 carbon atoms, halogen, —OCF$_3$, —CF$_3$ and SCF$_3$ and (c) heterocycle optionally subsubstituted with at least one member of the group consisting of —OH alkoxy of 1 to 8 carbon atoms, alkyl of 1 to 8 carbon atoms, halogen, —CF$_3$, —OCF$_3$ and —SCF$_3$, A is selected from the group consisting of optionally unsaturated alkyl of 1 to 18 carbon atoms, optionally unsaturated cycloalkyl of 3 to 18 carbon atoms and the remainder of an alcohol used in synthesis of pyrethrinoid esters, X is halogen and the ethylenic double bond may have Z or E geometry.

The compounds of formula I exist in isomeric forms due to the presence of asymmetric carbon atoms in the 1- and 3-positions of the ring, to other asymetric centers in the alcohol portions thereof and to the configuration of the double bond in the side chain in the 3-position as well as possible asymmetric centers in the A and R substituents.

Examples of A are alkyl such as methyl, ethyl, n-propyl, isopropyl, isobutyl, tert.-butyl and n-butyl or the remainder of an alcohol used in the synthesis of pesticidal esters of the biologically active pyrethrinoid series, preferably one of the list of radicals listed infra.

Among the preferred compounds of formula I are those wherein A is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

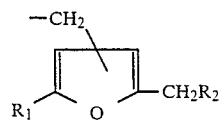 (3)

wherein R$_1$ is selected from the group consisting of hydrogen and methyl and R$_2$ is selected from the group consisting of —C≡CH and monocyclic aryl,

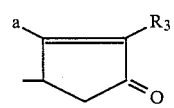 (4)

wherein a is selected from the group consisting of hydrogen and methyl and R$_3$ is an aliphatic group of 2 to 6 carbon atoms containing at least one carbon-carbon unsaturation,

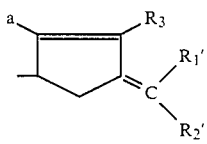 (5)

wherein a and R₃ have the above definition and $R_1'$ and $R_2'$ are individually selected from the group consisting of hydrogen, halogen, alkyl of 1 to 6 carbon atoms, aryl of 6 to 10 carbon atoms, cyano and alkoxy carbonyl of 2 to 5 carbon atoms,

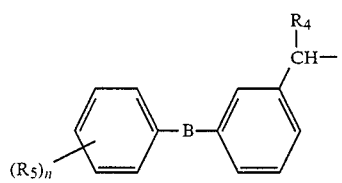 (6)

wherein B is selected from the group consisting of —CH₂—,

—O—, —S—, —R₄ is selected from the group consisting of hydrogen, —C≡N, —CH₃, —CONH₂, —CSNH₂ and —C≡CH, n is an integer from 0, 1 or 2 and R₅ is selected from the group consisting of halogen and —CH₃

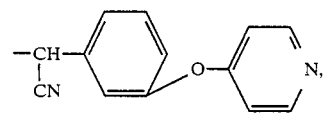 (7)

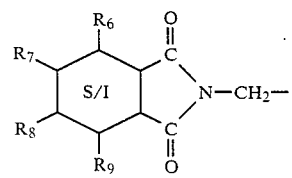 (8)

wherein R₆, R₇, R₈ and R₉ are selected from the group consisting of hydrogen, chlorine and methyl and S/I symbolizes an aromatic ring on dihydro, tetrahydro or hexahydro ring (9) succinimido-methylene or maleimido-methylene

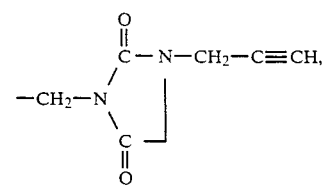 (10)

 (11)

wherein R₁₀ is selected from the group consisting of hydrogen and —CN, R₁₂ is selected from the group consisting of —CH₂— and —O— and R₁₁ is selected from the group consisting of thiazolyl and thiadiazolyl with the bond to $$-\overset{R_{10}}{\underset{|}{CH}}-$$

being in any one of the positions, R₁₂ being bonded to R₁₁ by the carbon atom included between a sulfur atom and a nitrogen atom,

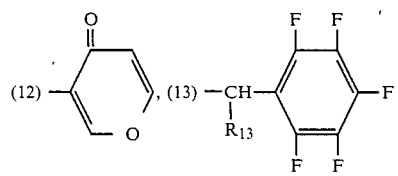

wherein R₁₃ is selected from the group consisting of hydrogen and —CN,

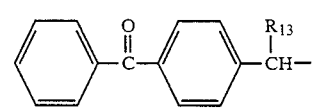 (14)

wherein R₁₃ has the above definition

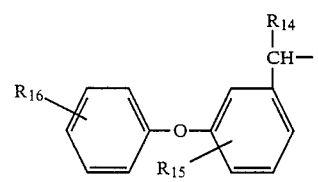 (15)

wherein R₁₄ is selected from the group consisting of hydrogen, methyl, ethynyl and —CN and R₁₅ is selected from the group consisting of fluorine, chlorine and bromine and R₁₆ is selected from the group consisting of hydrogen, chlorine, bromine and fluorine and

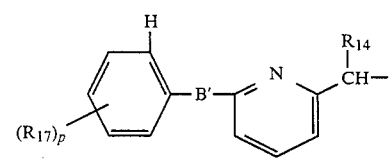 (16)

wherein R₁₄ has the above definition, p is 0, 1 or 2, each R₁₇ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF₃, 3,4-methylenedioxy, chlorine, bromine and fluorine, B' is selected from the group consisting of —O— and —S—.

An example of R₂ as monocyclic aryl is 5-benzyl-3-furyl-methyl and examples of R₃ are —CH₂—CH=CH₂, —CH₂—CH=CH—CH₃, —CH₂—CH=CH—CH₂—CH₃ and —CH₂—CH=CH—CH=CH₂. Examples of substituent (6) are 3-phenoxy-benzyl, α-cyano-3-phenoxy-benzyl, α-ethynyl-3-phenoxy-benzyl, 3-benzoyl-benzyl, 1-(3-phenoxyphenyl)-ethyl and α-thioamido-3-phenoxy benzyl.

When A is alkyl, it is preferably methyl, ethyl, n-propyl, isopropyl, n-butyl, isobutyl or tert-butyl and when A is benzyl substituted with at least one alkyl, the alkyls are preferably methyl or ethyl. When A is benzyl substituted with at least one alkenyl, the alkenyl is preferably vinyl, allyl, 2-methylallyl or isobutenyl. When A is benzyl substituted with alkadienyl, the alkadienyl preferably is allene or —CH=CH—CH=CH$_2$. When A is benzyl substituted with at least one alkenyloxy, it is preferably vinyloxy, allyloxy, 2-methylallyloxy or isobutenyloxy. When A is benzyl substituted with at least one halogen, the halogens are preferably fluorine, chlorine or bromine.

R$_2$ is preferably a phenyl and R$_1'$ and R$_2'$ are preferably fluorine, chlorine or bromine, methyl, ethyl, branched or linear hexyl, phenyl, methoxycarbonyl, ethoxycarbonyl and branched or linear pentoxycarbonyl. R$_5$ is preferably chlorine, fluorine or bromine.

R$_{17}$ is preferably methyl, ethyl, branched or linear butyl or butylthio or butoxy, methoxy, ethoxy, methylthio, ethylthio, methylsulfonyl, ethylsulfonyl or branched or linear butyl sulfonyl.

When R is saturated alkyl, it is preferably methyl, ethyl, isopropyl, n-propyl, n-butyl, sec.-butyl, isobutyl, n-pentyl, n-hexyl, tert.-butyl, branched or linear pentyl, hexyl, decyl, tetradecyl or octadecyl. When R is cycloalkyl, it is preferably cyclopropyl, cyclobutyl, cyclopentyl, cyclohexyl or cycloheptyl. When R is cycloalkylalkyl, it is preferably one of the above saturated alkyls substituted by cyclopropyl, cyclobutyl, cyclopentyl or cyclohexyl.

When R is an unsaturated alkyl, it is preferably ethenyl, propenyl, linear or branched butenyl, hexenyl, decenyl, tetradecenyl or octadecenyl or may be an unsaturated aliphatic with two or more double bonds.

When R is cycloalkyl substituted with at least one substituent, the substituent is selected from the group consisting of halogen, alkyl and alkoxy of 1 to 6 carbon atoms and —NO$_2$.

Examples of R as alkyl substituted with one or more functional groups are preferably alkyl of 1 to 8 carbon atoms such as methyl, ethyl, propyl, isopropyl, n-butyl, isobutyl or tert.-butyl substituted with at least one member of the group consisting of halogen, —OH, —SH, —OR' and —SR' and R' is selected from the group consisting of alkyl of 1 to 8 carbon atoms, —NO$_2$, —CN, —SO$_3$H, —PO$_4$H$_2$,

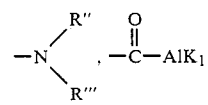

—SO$_2$AlK$_2$ and —SO$_3$AlK$_3$, R'' and R''' are individually selected from the group consisting of hydrogen and alkyl of 1 to 8 carbon atoms and AlK$_1$, AlK$_2$ and AlK$_3$ are alkyl of 1 to 18 carbon atoms.

R may also be alkyl substituted with an aryl group such as benzyl or phenethyl optionally substituted with at least one member of the group consisting of —OH, alkyl and alkoxy of 1 to 8 carbon atoms, halogen, —CF$_3$, —OCF$_3$, —SCF$_3$ and

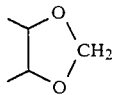

(G). R may also be alkyl substituted on two adjacent carbon atoms with the group

(G$_1$) or substituted with

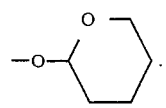

When R is an alkyl radical substituted by one or more functional groups, the preferred examples of R are (1) —(CH$_2$)$_n$—CHal$_3$ wherein n is an integer from 1 to 8 and Hal is a halogen, such as —CH$_2$—CCl$_3$, —CH$_2$—CF$_3$, —CH$_2$—CH$_2$—CCl$_3$ or —CH$_2$—CH$_2$—CF$_3$, (2) —(CH$_2$)$_{n1}$—CHHal$_2$ wherein n$_1$ is 0 to 8 and Hal is halogen such as —CH$_2$—CHCl$_2$, —CH$_2$—CHF$_2$ and —CHF$_2$, (3) —(CH$_2$)$_n$—CH$_2$Hal wherein Hal and n have the above definitions, such as —CH$_2$—CH$_2$—Cl or —CH$_2$—CH$_2$F, (4) —C—(CHal$_3$)$_3$ wherein Hal is a halogen, such as

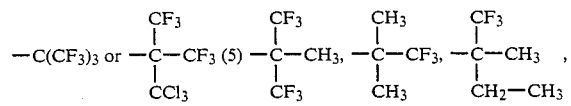

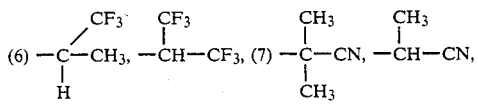

—(CH$_2$)$_n$—CN wherein n is 1 to 8,

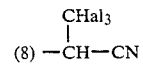

wherein Hal is a halogen, such as

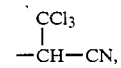

(9) (CH$_2$)$_n$—OR' wherein n has the above definition and R' is hydrogen or branched or linear alkyl of 1 to 8 carbon atoms such as —CH$_2$—OCH$_3$, —CH$_2$—CH$_2$—OCH$_3$, —CH$_2$CH$_2$—O—CH$_2$—CH$_3$ or —CH$_2$—CH$_2$—OH,

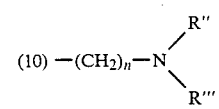

wherein n is 1 to 8 and R″ and R‴ are individually hydrogen or branched or linear alkyl of 1 to 8 carbon atoms such as—

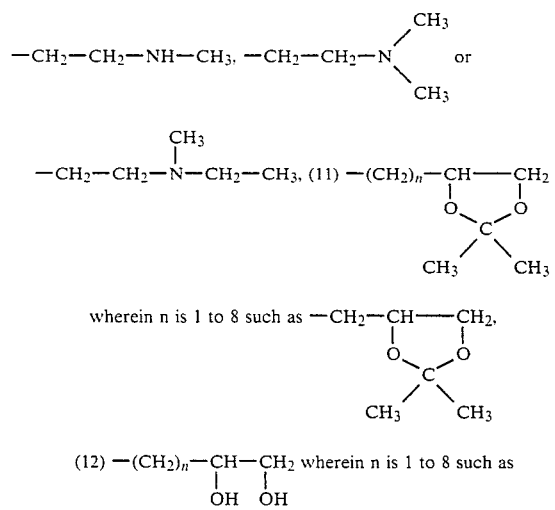

(12) —(CH₂)ₙ—CH—CH₂ wherein n is 1 to 8 such as
         |      |
         OH     OH —CH₂—CH—CH₂—OH, (13) —(CH₂)ₙ—O—[tetrahydropyran]

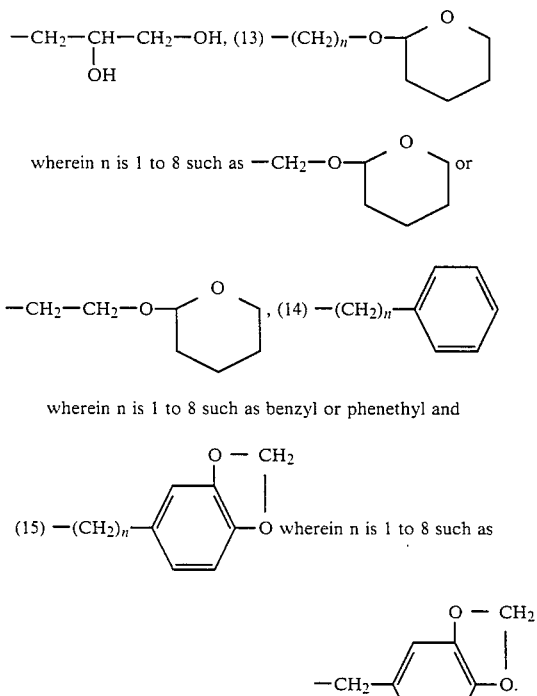

When R is an optionally substituted aryl, preferred examples are phenyl optionally substituted with at least one member of the group consisting of —OH, alkyl and alkoxy of 1 to 8 carbon atoms, halogen, —CF₃, —OCF₃ and —SCF₃. Examples of R as heterocycles as pyridinyl, furanyl, thiophenyl, oxazolyl and thiazolyl. The preferred halogens are fluorine, chlorine or bromine.

Among the compounds of the invention, the preferred compounds are those wherein the moiety of cyclopropanic acid have 1R,cis or 1R,trans configuration.

Among the preferred groups of A are α-cyano-3-phenoxybenzyl in the S,R or RS form, α-cyano 3-phenoxy 4-fluorobenzyl in the S,R ou RS form and cyano-(6-phenoxy-2-pyridyl)methyl in the S, R or R,S form. Other alcohols are illustrated in the following Table.

Examples of specific compounds of formula I are (S)α-cyano-3-phenoxy-benzyl(1R,cis,ΔE)2,2-dimethyl-3-[2-fluoro-3-oxo-3-isopropylthio-propenyl]-cyclopropane-carboxylate, (S)α-cyano-3-phenoxy-benzyl(1R,cis,ΔE)2,2-dimethyl-3-[2-fluoro-3-oxo-3-tert.-butylthio-propenyl]-cyclopropane-carboxylate, (S)α-cyano-3-phenoxy-benzyl(1R,cis,ΔE)2,2-dimethyl-3-[2-fluoro-3-oxo-3-ethylthio-propenyl]-cyclopropane-carboxylate, (S)α-cyano-3-phenoxy-benzyl(1R,cis,ΔE)2,2-dimethyl-3-[2-fluoro-3-oxo-3-methylthio-propenyl]-cyclopropane-carboxylate, (S)α-cyano-3-phenoxy-4-fluoro-benzyl(1R,cis,ΔE)2,2-dimethyl-3-[2-fluoro-3-oxo-3-isopropylthio-propenyl]-cyclopropane-carboxylate and (R,S)-cyano-(6-phenoxy-2-pyridyl)methyl(1R,cis,ΔE)2,2-dimethyl-3-[2-fluoro-3-oxo-3-isopropylthio-propenyl]-cyclopropane-carboxylate.

Additional compounds of formula I are illustrated in the following Table wherein the various volumes of X, R and A are given for the compounds.

| X | R | A |
|---|---|---|
| F | —C₂H₅ |  |
| ″ | ″ | 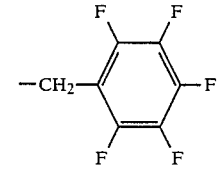 |
| ″ | ″ | 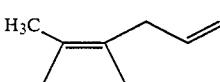 |
| ″ | ″ | 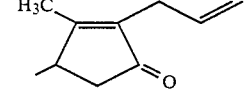 |
| ″ | ″ | 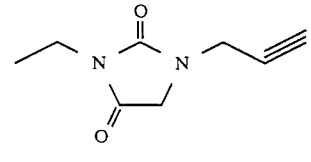 |
| ″ | ″ | 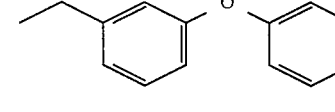 |
| ″ | ″ | 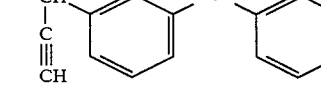 |
| ″ | ″ | 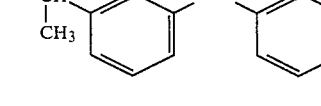 |
| ″ | —CH₃ | ″ |

| X | R | A |
|---|---|---|
| " | —CH$_2$CF$_3$ | " |
| " | —C$_2$H$_5$ | -CH(CN)-pyridine-O-phenyl |
| " | —n-propyl | " |
| " | —cyclopropyl | " |
| " | —(CH$_2$)$_2$OCH$_3$ | " |
| " | —CH$_2$—CH$_2$F | " |
| Cl | —CH$_3$ | " |
| " | —C$_2$H$_5$ | " |
| " | —n-propyl | -CH(CN)-phenyl-O-phenyl |
| " | —t Bu | " |
| " | —CH$_2$CF$_3$ | " |
| " | —CH$_3$ | -CH(CN)-(F-phenyl)-O-phenyl |
| " | —C$_2$H$_5$ | -CH(CN)-pyridine-O-phenyl |
| " | —CH$_3$ | " |
| " | " | N-ethyl-N'-propargyl hydantoin |
| " | —C$_2$H$_5$ | " |
| " | —t Bu | " |
| Br | —CH$_3$ | -CH(CN)-phenyl-O-phenyl |
| " | —C$_2$H$_5$ | " |
| " | —t Bu | " |
| " | —CH$_3$ | -CH(CN)-pyridine-O-phenyl |
| " | —C$_2$H$_5$ | " |
| " | —CH$_3$ | -CH(CN)-(F-phenyl)-O-phenyl |
| " | —CH$_3$ | N-ethyl-N'-propargyl hydantoin |
| " | —C$_2$H$_5$ | " |
| " | —t Bu | " |
| " | 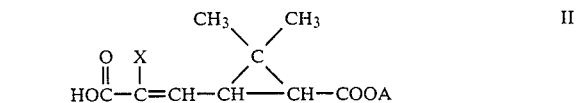 | " |

The novel process of the invention for the preparation of a compound of formula I comprises reacting a compound of the formula

$$\underset{HOC}{\overset{O}{\|}}-\underset{|}{\overset{X}{C}}=CH-CH\underset{}{\diagdown}CH-COOA \qquad II$$

wherein X and A have the above definition in an organic solvent in the presence of dicyclohexylcarbodiimide with a mercaptan of the formula

R—SH    III wherein R has the above definition.

Examples of suitable solvents are methylene chloride, benzene and tetrahydrofuran and the reaction is preferably effected in the presence of 4-dimethylamino-pyridine. If the compound of formula III has other functinal groups capable of reacting with the acid of formula II, it is necessary to first block these groups.

The acids of formula II are described in French Pat. No. 2,491,060, or EPO application Ser. No. 0,050,534.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

Certain of the compounds of formula I possess an excellent lethal power and a very good knock-down power and the products of Examples 1,2,3,4,7 and 8 are particularly remarkable on this point. The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene(piperonyl butoxide) or N-(2-ethyl-heptyl)-bicyclo-[2,2-1]5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene-methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxybenzyl alcohol with 2-p-chlorophenyl-2-isopropyl-acetic acids, esters of allethrolone, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(S)α-cyano-3-phenoxy-benzyl(1R,cis,ΔE)2,2-dimethyl-3-[2-fluoro-3-oxo-3-isopropylthio-propenyl]-cyclopropane-carboxylate A solution of 25 mg of 4-dimethylamino-pyridine, 1.2 g of dicyclohexylcarbodiimide and 5 ml of methylene chloride was added at 5° C. to a mixture of 2.2 g of (S)α-cyano-3-phenoxy-benzyl(1R,cis,ΔE)2,2-dimethyl-3-[2-fluoro-3-oxo-3-hydroxy-propenyl]-cyclopropane-carboxylate [prepared in EPO application Ser. No. 0,050,534], 2 ml of 2-propanethiol and 5 ml of methylene chloride and the mixture was stirred at 5° C. for one hour, at 20° C. for 2 hours and was filtered. The filtrate was evaporated to dryness under reduced pressure and the residue was chromatographed over silica gel. Elution with an 8-2 hexane-ethyl acetate mixture yielded 1.216 g of (S)α-cyano-3-phenoxy-benzyl(1R,cis,ΔE)2,2-dimethyl-3-[2-fluoro-3-oxo-3-isopropylthio-propenyl]-cyclopropane-carboxylate melting at 70° C. and having a specific rotation of $[\alpha]_D^{20} = +66°$ (c=0.6% in chloroform).

NMR Spectrum (deuterochloroform)

Peaks at 1.22–1.28 ppm (hydrogens of geminal methyls); at 1.32–1.43 ppm (hydrogens of methyls of isopropyl); at 1.9–2.05 ppm (1-hydrogen of cyclopropyl); at 2.9–3.3 ppm (3-hydrogen of cyclopropyl); at 3.8 ppm (2-hydrogen of isopropyl); at 5.9–6.1–6.2–6.4 ppm (ethylenic hydrogen); at 6.4 ppm (hydrogen of carbon α-to —CN); at 7–7.7 ppm (aromatic hydrogens).

EXAMPLE 2

(S)α-cyano-3-phenoxy-benzyl(1R,cis,ΔE)2,2-dimethyl-3-[2-fluoro-3-oxo-3-tert.-butylthio-propenyl]-cyclopropane-carboxylate Using the procedure of Example 1, 3 g of the said ester and 2 ml of tert.-butanethiol were reacted to obtain after chromatography over silica gel and elution with a 9-1 hexane-ethyl acetate mixture 1.04 g of (S)α-cyano-3-phenoxybenzyl(1R,cis,ΔE)2,2-dimethyl-3-[2-fluoro-3-oxo-3-tert.-butylthio-propenyl]-cyclopropane-carboxylate with a specific rotation of $[\alpha]_D^{20} = +84° \pm 3°$ (c=0.5% in chloroform).

EXAMPLE 3

Using the procedure of Example 1, 3 g of the said ester and 1.5 ml of ethanethiol were reacted to obtain after chromatography over silica gel and elution with an 80-20 hexane-ethyl acetate mixture 1.3 g of (S)α-cyano-3-phenoxybenzyl(1R,cis,ΔE)2,2-dimethyl-3-[2-fluoro-3-oxo-3-ethylthiopropenyl]-cyclopropane-carboxylate with a specific rotation of $[\alpha]_D^{20} = +66.5° \pm 2.5°$ (c=0.5% in chloroform).

EXAMPLE 4

Using the procedure of Example 1, 3 g of the said ester and 4 g of methanethiol were reacted to obtain after chromatography over silica gel and elution with a 9-1-hexaneethyl acetate mixture 1.14 g of (S)α-cyano-phenoxy-benzyl(1R,cis,ΔE)2,2-dimethyl-3-[2-fluoro-3-oxo-3-methylthiopropenyl]-cyclopropane-carboxylate with a specific rotation of $[\alpha]_D^{20} = +60° \pm 1.5°$ (c=1% in chloroform).

EXAMPLE 5

(S)α-cyano-3-phenoxy-benzyl(1R,cis,ΔE)2,2-dimethyl-3-[2-bromo-3-oxo-3-isopropylthio-propenyl]-cyclopropane-carboxylate Step A:
(S)α-cyano-3-phenoxy-benzyl(1R,cis,ΔE)2,2-dimethyl-3-[2-bromo-3-oxo-3-hydroxy-propenyl]-cyclopropane-carboxylate A mixture of 4 g of (S)α-cyano-3-phenoxy-benzyl(1R,cis,ΔE)2,2-dimethyl-3-[2-bromo-3-oxo-3-tert.-butoxypropenyl]-cyclopropane-carboxylate [described in EPO application Ser. No. 0,050,534], 50 ml of toluene and 0.4 g of p-toluene sulfonic acid was heated at 130°–140° C. for 25 minutes and was cooled to 20° C. Water was added to the mixture and the decanted organic phase was washed with water, dried and evaporated to dryness under reduced pressure. The residue was chromatographed over silica gel and was eluted with a 70-30-1 hexane-ethyl acetate-acetic acid mixture to obtain 3.6 g of (S)α-cyano-3-phenoxy-benzyl(1R,cis,-ΔE)2,2-dimethyl-3-[2-bromo-3-oxo-3-hydroxy-propenyl]-cyclopropane-carboxylate.

STEP B:
(S)α-cyano-3-phenoxy-benzyl(1R,cis,ΔE)2,2-dimethyl-3-[2-bromo-3-oxo-3-isopropylthio-propenyl]-cyclopropane-carboxylate Using the procedure of Example 1, 3.6 g of the ester of Step A and 5 ml of 2-propanethiol were reacted to obtain after chromatography over silica gel and eluted with benzene 1.3 g of (S)α-cyano-3-phenoxy-benzyl(1R,cis,ΔE)2,2-dimethyl-3-[2-bromo-3-oxo-3-isopropylthio-propenyl]-cyclopropane-carboxylate with a specific rotation of $[\alpha]_D° = +56.5° \pm 2.5°$ (c=0.7% in toluene) and melting at 99° C.

EXAMPLE 6

(S)α-cyano-3-phenoxy-benzyl(1R,cis,ΔE)2,2-dimethyl-3-[2-chloro-3-oxo-3-ispropylthio-propenyl]-cyclopropane-carboxylate Using the procedure of Step A of Example 5, 3 g of (S)-α-cyano-3-phenoxy-benzyl(1R,cis,ΔE)2,2-dimethyl-3-[2-chloro-3-oxo-3-tert.-butoxy-propenyl]-cyclopropane-carboxylate [described in EPO application Ser. No. 0,050,534 were reacted to obtain 2.5 g of (S)α-cyano-3-phenoxy-benzyl(1R,cis,ΔE)2,2-dimethyl-3-[2-chloro-3-oxo-3-hydroxy-propenyl]-cyclopropane-carboxylate.

Using the procedure of Example 1, 2.3 g of the said ester and 5 ml of 2-propanethiol were reacted to obtain after chromatography over silica gel and elution with a 1—1 benzene-hexane mixture 1.2 g of (S)α-cyano-3-phenoxy-benzyl(1R,cis,ΔE)2,2-dimethyl-3-[2-chloro-3-oxo-3-isopropylthiopropenyl]-cyclopropane-carboxylate melting at 101°–102° C. and having a specific rotation of $[\alpha]_D° = +70° \pm 2°$ (c=1% in toluene).

EXAMPLE 7

Using the procedure of Example 1, 3.6 g of (S)α-cyano-3-phenoxy-4-fluoro-benzyl(1R,cis,ΔE)2,2-dimethyl-3-[2-fluoro-3-oxo-3-hydroxy-propenyl]-cyclopropane-carboxylate [described in EPO application Ser. No. 0,050,534] and 1 ml of 2-propanethiol were reacted to obtain after chromatography over silica gel and elution with an 8-2 hexane-ethyl acetate mixture 1.9 g of (S)α-cyano-3-phenoxy-4-fluoro-benzyl(1R,cis,ΔE)2,2-dimethyl-3-[2-fluoro-3-oxo-3-isopropylthio-propenyl]-cyclopropane-carboxylate melting at 110° C. and having a specific rotation of $[\alpha]_D^{20} = +73° \pm 3°$ (c=0.5% in chloroform).

EXAMPLE 8

(R,S)α-cyano-(6-phenoxy-2-pyridyl)-methyl(1R,cis,-ΔE)2,2-dimethyl-3-[2-fluoro-3-oxo-3-isopropylthio-propenyl]-cyclopropane-carboxylate

STEP A:
(R,S)α-cyano-(6-phenoxy-2-pyridyl)-methyl(1R,cis,-ΔE)2,2-dimethyl-3-[3-fluoro-3-oxo-3-tert.-butoxy-propenyl]-cyclopropane-carboxylate 0.04 g of 4-dimethylamino-pyridine and 1.6 g of dicyclohexylcarbodiimide were added with stirring at 5° C. to a mixture of 1.75 g of (R,S)α-cyano-(6-phenoxy-2-pyridyl)methyl alcohol, 2 g of (1R,cis,ΔE)2,2-dimethyl-3-[2-fluoro-3-oxo-3-tert.-butoxy-propenyl]-cyclopropane-carboxylic acid [described in EPO application Ser. No. 0,050,534] and 20 ml of methylene chloride and the mixture was stirred at 20° C. for 4 hours and was filtered. The filtrate was evaporated to dryness and the residue was chromatographed over silica gel. Elution with an 8-2 hexane-ethyl acetate mixture yielded 3.52 g of (R,S)α-cyano-(6-phenoxy-2-pyridyl)-methyl(1R,cis,-ΔE)2,2-dimethyl-3-[3-fluoro-3-oxo-3-tert.-butoxy-propenyl]-cyclopropane-carboxylate.

STEP B:
(R,S)α-cyano-(6-phenoxy-2-pyridyl)-methyl(1R,cis,-ΔE)2,2-dimethyl-3-[2-fluoro-3-oxo-3-isopropylthio-propenyl]-cyclopropane-carboxylate A mixture of 3.5 g of the product of Step A, 50 ml of toluene and 0.5 g of p-toluene sulfonic acid was refluxed until gas evolution ceased and was cooled and filtered. The filtrate was evaporated to dryness to obtain 2.8 g of (R,S)α-cyano-(6-phenoxy-2-pyridyl)-methyl(1R,cis,-ΔE)2,2-dimethyl-3-[2-fluoro-3-oxo-3-hydroxy-propenyl]-cyclopropane-carboxylate which was used as is.

Using the procedure of Example 1, 2.8 g of the said product and 1 ml of 2-propanethiol were reacted to obtain after chromatography over silica gel and elution with an 8-2 hexane-ethyl acetate mixture 1.23 g of (R,S)α-cyano-(6-phenoxy-2-pyridyl)-methyl(1R-,cis,ΔE) 2,2-dimethyl-3-[2-fluoro-3-oxo-3-isopropylthio-propenyl]-cyclopropane-carboxylate with a specific rotation of $[\alpha]_D° +75°±4°$ (c=0.3% in chloroform).

EXAMPLE 9

A soluble concentrate was prepared by homogenously mixing 0.25 g of the product of Example 1, 1 g of piperonyl butoxide, 0.25 g of Tween 80, 0.1 g of Topanol A and 98.4 g of water.

An emulsifiable concentrate was prepared by intimately mixing 0.015 g of the product of Example 3, 0.5 g of piperonyl butoxide, 0.1 g of Topanol A, 3.5 g of Tween 80 and 95.885 g of xylene.

A second emulsifiable concentrate was prepared by homogeneously mixing 1.5 g of the product of Example 7, 20 g of Tween 80, 0.1 g of Topanol A and 78.4 g of xylene.

A fumigant composition was prepared by homogenously mixing 0.25 g of the product of Example 7, 25 g of tabu powder, 40 g of powdered cedar needles, 33.75 g of pine wood powder. 0.5 g of brillant green and 0.5 g of p-nitrophenol.

A solution of a veterinary composition was prepared containing 5 g of the compound of Example 1, 25 g of piperonyl butoxide, 10 g of Polysorbate 80, 25 g of Triton×100, 1 g of tocophenol acetate and sufficient ethanol for 100 ml of solution. The solution was diluted with 5 liters of water just before use.

TEST DATA

A. Lethal activity against houseflies

Female houseflies 4 to 5 days old were used in the test by topical application of 1 μl of an acetone solution of the test compound on the dorsal thorax of the insects with an Arnold micro manipulator. 50 insects were used for each dose and the readings of number of dead flies was taken 24 hours after treatment to determine the $DL_{50}$ or dose in nanograms necessary to kill 50% of the insects. The $DL_{50}$ for the compounds of Examples 1,3,7 and 8 was 1.12, 0.5.,0.65 and 1.9 in ng per insect, respectively.

B. Lethal Activity against beetles

The test was effected by contact with a film on glass by depositing an acetone solution of the test compounds at different concentrations on the bottom of a glass Petri dish whose edges were covered with talc to prevent the escape of the insects. The $CL_{50}$ or lethal concentration in mg/m² at which 50% of the beetles were killed for the compounds of Examples 1 and 2 was 0.23 and 0.20, respectively.

C. Knock-down effect on houseflies 4 day old female houseflies were directly sprayed in a Kearns and March chamber at a concentration of 0.25 g/l in a mixture of Isopar L (petroleum solvent) containing 5% acetone using 2 ml in one second. 50 insects were used for each test and reading were taken each minute for 10 minutes and then at 15 minutes to determine the $KT_{50}$ in minutes by the known method. The $KT_{50}$ for the compounds of Examples 1,3,4 and 8 was 11.3, 3.9, 5.4 and 6.0 respectively.

D. Lethal activity against Spodoptera Littoralis Larvae

The test was effected by topical application with an Arnold micro manipulator of an acetone solution of the test compound to the dorsal thorax of the larvae which were in the fourth stage of larvae development or about 10 days old at 24° C. and 65% relative humidity. After treatment, the larvae were placed in artifical nutritive media and the $DL_{50}$ in nanograms per insect were determined. The $DL_{50}$ for the compounds of Examples 1,3,4 and 7 was 12.3, 2.5, 5.4 and 5.6 respectively.

E. Lethal Activity against Acanthocelide Subjectus

The procedure of test D was repeated with Acanthocelide subjectus to determine the $DL_{50}$ in ng per insect. The $DL_{50}$ for the compounds of Examples 1,2,3,4 and 7 was 5.86, 1.82, 1.86, 3.74 and 0.49 respectively.

F. Lethal Activity against Aphis Cracivora 10 7 day old adult Aphis Cracivora were used for each concentration of the contact-ingestion method. Bean leaves were treated with 2 ml of acetone solution of the test compound spraying 1 ml with a Fisher pistol on each side. The leaf was placed in a plastic Petri dish with a damp circle of paper and dried after which the insects were placed in the dish. The insects were left in contact with the leaf for one hour and untreated leaves were used as controls. The number of dead insects after 24 hours was determined to calculate the $CL_{50}$ dose in mg/hl. The $CL_{50}$ dose for the compounds of Examples 1,2,7 and 8 was 0.6, 1.3, 1.0 and 1.8 respectively.

G. Acaricidal Activity against Tetranychus urticae

Bean plants containing 2 leaves were infested with 25 female Tetranychus urticae per leaf and were then placed under a ventilated cover with a constant light. The plants were treated with a Fisher pistol with 4 ml of a toxic solution per plant in a 1—1 water-acetone mixture and were allowed to dry for 12 hours before infestation. The reading of dead insects was taken after 80 hours to determine the $CL_{50}$ in mg/hl. The $CL_{50}$ for the compounds of Examples 1 and 7 was 424 and 938 respectively.

The above data shows that the compounds of formula I have a good insecticidal and a good acaricidal activity.

Various modifications of the compounds and methods of the invention may be made without departing from the spirit or scope thereof and it is to be understood that the invention is intended to be limited only as defined in the appended claims.

What we claim is:

1. An ester in all possible isomeric forms and mixtures thereof of the formula

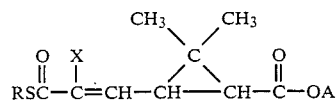   I wherein R is selected from the group consisting of (a) alkyl of 1 to 18 carbon atoms, alkenyl and alkynyl of 1 to 18 carbon atoms, and cycloalkyl, or cycloalkenyl or cycloalkenylalkyl or cycloalkylalkyl of 3 to 8 carbon atoms cycloalkyl, cycloalkenyl, cycloalkylalkyl and cycloalkenylalkyl of 3 to 8 carbon atoms substituted with at least one member of the group consisting of halogen, —OH, —SH, —OR', —SR',

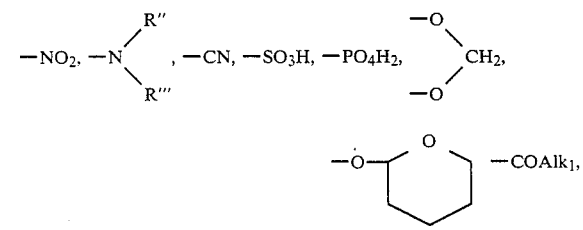

—SO$_2$Alk$_2$, —SO$_3$Alk$_3$, aryl, aryl substituted with at least one member of the group consisting of —OH, alkoxy of 1 to 8 carbon atoms, alkyl of 1 to 8 carbon atoms, halogen, —CF$_3$, —OCF$_3$, —SCF$_3$ and

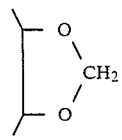

R' is alkyl of 1 to 8 carbon atoms, R" and R''' are individually selected from the group consisting of hydrogen and alkyl of 1 to 8 carbon atoms, Alk$_1$, Alk$_2$ and Alk$_3$ are individually alkyl of 1 to 18 carbon atoms (b) aryl of 6 to 14 carbon atoms, aryl substituted with at least one substituent selected from the group consisting of —OH, alkoxy of 1 to 8 carbon atoms, alkyl of 1 to 8 carbon atoms, halogen, —OCF$_3$, —CF$_3$ and —SCF$_3$ and (c) heterocycle, heterocycle substituted with at least one member of the group consisting of —OH, alkoxy of 1 to 8 carbon atoms, alkyl of 1 to 8 carbon atoms, halogen, —CF$_3$, —OCF$_3$, and —CF$_3$, A is selected from the group consisting of alkyl of 1 to 18 carbon atoms, alkenyl and alkynyl of 2 to 18 carbon atoms cycloalkyl of 3 to 18 carbon atoms and cycloalkenyl of 3 to 18 carbon atoms and the remainder of an alcohol used in synthesis of pyrethrinoid esters, X is halogen and the ethylenic double bond may have Z or E geometry.

2. A compound of claim 1 wherein A is selected from the group consisting of (1) alkyl of 1 to 18 carbon atoms, (2) benzyl and benzyl substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

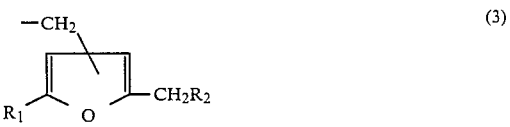   (3)

wherein R$_1$ is selected from the group consisting of hydrogen and methyl and R$_2$ is selected from the group consisting of —C≡CH and monocyclic aryl,

   (4)

wherein a is selected from the group consisting of hydrogen and methyl and R$_3$ is an aliphatic group of 2 to 6 carbon atoms containing at least one carbon-carbon unsaturation,

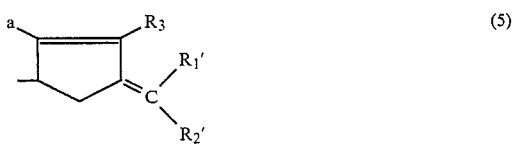   (5)

wherein a and R$_3$ have the above definition and R$_1$' and R$_2$' are individually selected from the group consisting of hydrogen, halogen, alkyl of 1 to 6 carbon atoms, aryl of 6 to 10 carbon atoms, cyano and alkoxy carbonyl of 2 to 5 carbon atoms,

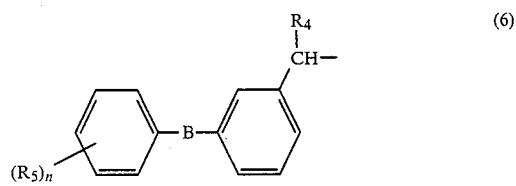   (6)

wherein B is selected from the group consisting of

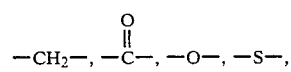

—R$_4$ is selected from the group consisting of hydrogen, —C≡N, —CH$_3$, —CONH$_2$, —CSNH$_2$ and —C≡CH, n is an integer from 0,1 or 2 and $R_5$ is selected from the group consisting of halogen and —$CH_3$

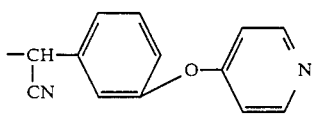 (7)

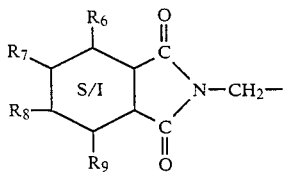 (8)

wherein $R_6$, $R_7$, $R_8$ and $R_9$ are selected from the group consisting of hydrogen, chlorine and methyl and S/I symbolizes an aromatic ring or dihydro, tetrahydro or hexahydro ring, (9) succinimido-methylene or maleimido-methylene

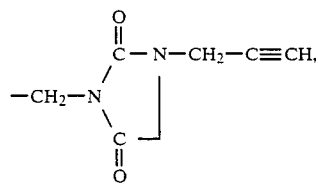 (10)

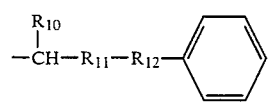 (11)

wherein $R_{10}$ is selected from the group consisting of hydrogen and —CN, $R_{12}$ is selected from the group consisting of —$CH_2$— and —O— and $R_{11}$ is selected from the group consisting of thiazolyl and thiadiazolyl with the bond to

being in any one of the positions, $R_{12}$ being bonded to $R_{11}$ by the carbon atom included between a sulfur atom and a nitrogen atom,

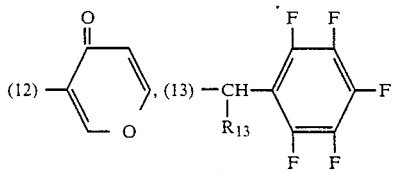 (12), (13)

wherein $R_{13}$ is selected from the group consisting of hydrogen and —CN,

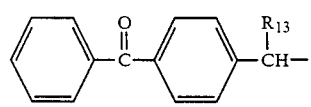 (14)

wherein $R_{13}$ has the above definition

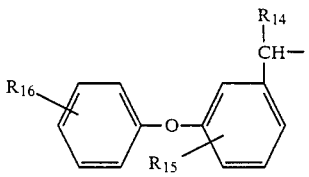 (15)

wherein $R_{14}$ is selected from the group consisting of hydrogen, methyl, ethynyl and —CN and $R_{15}$ is selected from the group consisting of fluorine, chlorine and bromine and $R_{16}$ is selected from the group consisting of hydrogen, chlorine, bromine and fluorine and

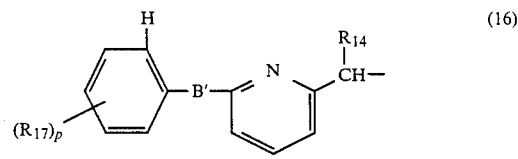 (16)

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —$CF_3$, 3,4-methylenedioxy, chlorine, bromine and fluorine, B' is selected from the group consisting of —O— and —S—.

3. The compound of claim 1 wherein the cyclopropane acid moiety has the (1R,trans) or (1R,cis) configuration.

4. A compound of claim 1 wherein A is selected from the group consisting of α-cyano-3-phenoxy-benzyl in the S,R and RS form, α-cyano-3-phenoxy-4-fluoro-benzyl in the S,R or RS form and α-cyano-(6-phenoxy-2-pyridyl) methyl in the S,R or R,S form.

5. A compound of claim 1 wherein X is fluorine.

6. A compound of claim 1 wherein X is bromine.

7. A compound of claim 1 wherein X is chlorine.

8. A compound of claim 1 selected from the group consisting of (S)α-cyano-3-phenoxy-benzyl(1R,cis,-ΔE)2,2-dimethyl-3-[2-fluoro-3-oxo-3-isopropylthio-propenyl]-cyclopropane-carboxylate, (S)α-cyano-3-phenoxy-benzyl(1R,cis,ΔE)2,2-dimethyl-3-[2-fluoro-3-oxo-3-tert.-butylthio-propenyl]-cyclopropane-carboxylate, (S)α-cyano-3-phenoxy-benzyl(1R,cis,ΔE)2,2-dimethyl-3-[2-fluoro-3-oxo-3-ethylthio-propenyl]-cyclopropane-carboxylate, (S)α-cyano-3-phenoxy-benzyl(1R,cis,ΔE)2,2-dimethy-3-[2-fluoro-3-oxo-3-methylthio-propenyl]-cyclopropane-carboxylate, (S)α-cyano-3-phenoxy-4-fluoro-benzyl(1R,cis,ΔE)2,2-dimethyl-3-[2-fluoro-3-oxo-3-isopropylthiopropenyl]-cyclopropane-carboxylate and (R,S)-cyano-(6-phenoxy-2-pyridyl)-methyl(1R,cis,ΔE)2,2-dimethyl-3-[2-fluoro-3-oxo-3-isopropylthio-propenyl]-cyclopropane-carboxylate.

9. An insecticidal composition comprising an insecticidally effective amount of at least one compound of claim 1 and an inert carrier.

10. A composition of claim 9 wherein A is selected from the group consisting of (1) alkyl of 1 to 18 carbon atoms, (2) benzyl and benzyl substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

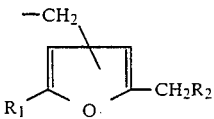 (3)

wherein $R_1$ is selected from the group consisting of hydrogen and methyl and $R_2$ is selected from the group consisting of —C≡CH and monocyclic aryl,

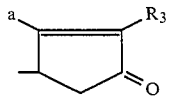 (4)

wherein a is selected from the group consisting of hydrogen and methyl and $R_3$ is an aliphatic group of 2 to 6 carbon atoms containing at least one carbon-carbon unsaturation,

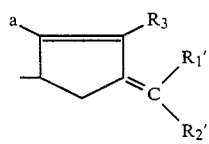 (5)

wherein a and $R_3$ have the above definition and $R_1'$ and $R_2'$ are individually selected from the group consisting of hydrogen, halogen, alkyl of 1 to 6 carbon atoms, aryl of 6 to 10 carbon atoms, cyano and alkoxy carbonyl of 2 to 5 carbon atoms,

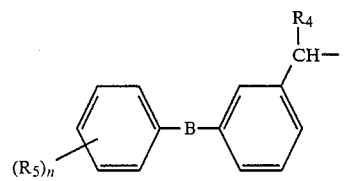 (6)

wherein B is selected from the group consisting of —CH$_2$—,

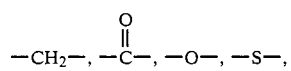

—$R_4$ is selected from the group consisting of hydrogen, —C≡N, —CH$_3$, —CONH$_2$, —CSNH$_2$ and —C≡CH, n is an integer from 0,1 or 2 and $R_5$ is selected from the group consisting of halogen and —CH$_3$

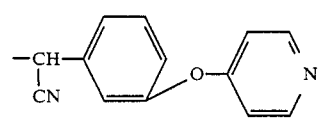 (7)

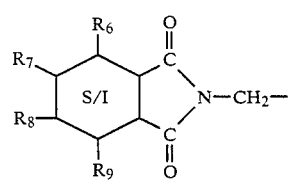 (8)

wherein $R_6$, $R_7$, $R_8$ and $R_9$ are selected from the group consisting of hydrogen, chlorine and methyl and S/I symbolizes an aromatic ring or dihydro, tetrahydro or hexahydro ring, (9) succinimido-methylene or maleimido-methylene

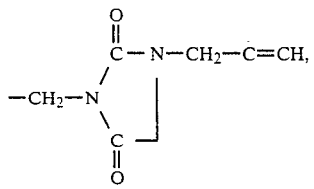 (10)

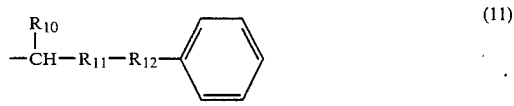 (11)

wherein $R_{10}$ is selected from the group consisting of hydrogen and —CN, $R_{12}$ is selected from the group consisting of —CH$_2$— and —O— and $R_{11}$ is selected from the group consisting of thiazolyl and thiadiazolyl with the bond to

being in any one of the positions, $R_{12}$ being bonded to $R_{11}$ by the carbon atom included between a sulfur atom and a nitrogen atom,

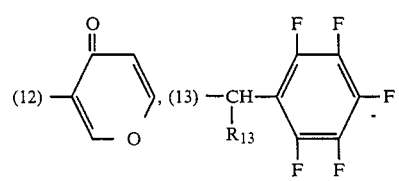

wherein $R_{13}$ is selected from the group consisting of hydrogen and —CN,

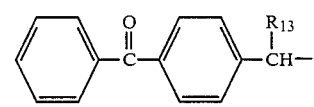 (14)

wherein $R_{13}$ has the above definition

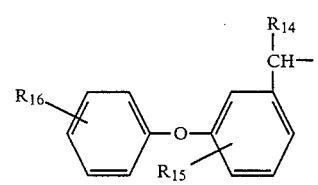 (15)

wherein $R_{14}$ is selected from the group consisting of hydrogen, methyl, ethynyl and —CN and $R_{15}$ is selected from the group consisting of fluorine, chlorine and bromine and $R_{16}$ is selected from the group consisting of hydrogen, chlorine, bromine and fluorine and

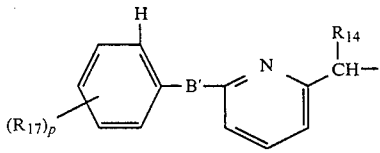
(16)

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, bromine and fluorine, B' is selected from the group consisting of —O— and —S—.

11. A composition of claim 9 wherein the cyclopropane acid moiety has the (1R,trans) or (1R,cis) configuration.

12. A composition of claim 9 wherein A is selected from the group consisting of α-cyano-3-phenoxy-benzyl in the S,R and RS form, α-cyano-3-phenoxy-4-fluoro-benzyl in the S,R or RS form and -cyano-(6-phenoxy-2-pyridyl)-methyl in the S,R or R,S form.

13. A composition of claim 9 wherein X is fluorine.

14. A composition of claim 9 wherein X is bromine.

15. A composition of claim 9 wherein X is chlorine.

16. A composition of claim 9 wherein the active compound is at least one member of the group consisting of (S)α-cyano-3-phenoxy-benzyl(1R,cis,ΔE)2,2-dimethyl-3-[2-fluoro-3-oxo-3-isopropylthio-propenyl]-cyclopropane-carboxylate, (S)α-cyano-3-phenoxy-benzyl(1R,cis,ΔE)2,2-dimethyl-3-[2-fluoro-3-oxo-3-tert.-butylthio-propenyl]-cyclopropane-carboxylate, (S)α-cyano-3-phenoxy-benzyl(1R,cis,ΔE)2,2-dimethyl-3-[2-fluoro-3-oxo-3-ethylthio-propenyl]-cyclopropane-carboxylate, (S)α-cyano-3-phenoxy-benzyl(1R,cis,ΔE)2,2-dimethyl-3-[2-fluoro-3-oxo-3-methylthio-propenyl]-cyclopropane-carboxylate, (S)α-cyano-3-phenoxy-4-fluoro-benzyl(1R,cis,ΔE)2,2-dimethyl-3-[2-fluoro-3-oxo-3-isopropylthio-propenyl]-cyclopropane-carboxylate and (R,S)-cyano-(6-phenoxy-2-pyridyl)-methyl(1R,cis,ΔE)2,2-dimethyl-3-[2-fluoro-3-oxo-3-isopropylthio-propenyl]-cyclopropane-carboxylate.

17. A composition of claim 9 also containing a pyrethrinoid synergist selected from the group consisting of piperonyl butoxide, N-(2-ethyl-heptyl)-bicyclo-[2,2-1]5-heptene-2,3-dicarboximide and tropital.

18. A composition of claim 9 also containing as a second active ingredient at least one prethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidenemethyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxybenzyl alcohol with 2-p-chlorophenyl-2-isopropyl-acetic acids, esters of allethrolones, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of claim 1 and the above pyrethrinoid esters are in all possible stereoisomer forms.

* * * * *